US006262255B1

(12) United States Patent
Mares-Guia

(10) Patent No.: US 6,262,255 B1
(45) Date of Patent: Jul. 17, 2001

(54) NON-IMMUNOGENIC, BIOCOMPATIBLE MACROMOLECULAR MEMBRANE COMPOSITIONS, AND METHODS FOR MAKING THEM

(75) Inventor: Marcos Mares-Guia, Miami, FL (US)

(73) Assignee: BIOMM, Inc., Miami, FL (US)

( * ) Notice: Subject to any disclaimer, the term of this patent is extended or adjusted under 35 U.S.C. 154(b) by 0 days.

(21) Appl. No.: 08/417,652

(22) Filed: Apr. 5, 1995

(51) Int. Cl.$^7$ .......................... C08B 37/00; A61K 31/715
(52) U.S. Cl. .......................... 536/53; 536/54; 536/55.1; 536/55.3; 536/56; 536/123.1; 536/124; 514/54; 514/57; 424/443; 424/488
(58) Field of Search .................. 514/54, 56, 57; 536/21, 53, 54, 56, 55.1, 123.1, 55.3, 124; 424/443, 488

(56) References Cited

U.S. PATENT DOCUMENTS

| 4,060,081 | 11/1977 | Yannas et al. | 602/49 |
|---|---|---|---|
| 4,378,224 | 3/1983 | Nimni et al. | 8/94.11 |
| 4,409,331 | 10/1983 | Lim | 435/178 |
| 4,585,754 | 4/1986 | Meisner et al. | 514/8 |
| 4,637,994 | * 1/1987 | Tani et al. | 502/404 |
| 4,704,131 | 11/1987 | Noishiki et al. | 623/66 |
| 4,944,767 | 7/1990 | Barbucci et al. | 623/66 |
| 4,945,086 | 7/1990 | Benitz et al. | 514/56 |
| 4,955,893 | 9/1990 | Yannas et al. | 606/154 |
| 4,979,959 | 12/1990 | Guire | 623/66 |
| 5,017,229 | * 5/1991 | Burns et al. | 106/162 |
| 5,024,841 | 6/1991 | Chu et al. | 424/422 |
| 5,071,436 | 12/1991 | Huc et al. | 623/16 |
| 5,108,438 | 4/1992 | Stone | 623/17 |
| 5,116,374 | 5/1992 | Stone | 623/16 |
| 5,129,877 | 7/1992 | Gallo et al. | 600/12 |
| 5,152,784 | 10/1992 | Tsilibary | 623/1 |
| 5,166,187 | 11/1992 | Collombel et al. | 514/21 |
| 5,169,631 | 12/1992 | Rase et al. | 424/401 |
| 5,244,672 | 9/1993 | Huc et al. | 424/450 |
| 5,252,339 | 10/1993 | Cristofori et al. | 424/479 |
| 5,258,043 | 11/1993 | Stone | 623/66 |
| 5,263,992 | 11/1993 | Guire | 623/66 |

FOREIGN PATENT DOCUMENTS

0531733 * 3/1993 (EP) .
91/19521 * 12/1991 (WO) .

OTHER PUBLICATIONS

Fluka Catalog, p. 866, Fluka Chemie AG, 1995.*
Shimda et al. In "Cellul.: Chem., Biochem. Mater. Aspects", 1993, J. F. Kennedy, editor; Chapter 59, 409–414.*
International Report (1984) Businessweek, Nov. 2, p.46–50.
Bylinsky, G. (1984) Fortune, Aug. 6, p.40–43.
Chang, T.M.S. (1976) Meth. Enzymol. 44, 676–698.
Chang, T.M.S. (1984) in Microencapsulation and Artificial Cells, T.M.S. Chang, editor, Humana Press, Clifton, N.J., p.3–24.
Howell, S.L., Ishaq, S. and Tyhurst, M. (1982) J. Physiol. 324, 20P–21P.
Tze, W.J. and Tai, J. (1982) Transplantation 33, 563–564.
Abstract of Thomas M.S. Chang, and Wong, H. (1992) U.S. Patent No. 5,084,350 from American Chemical Society (1993).
Abstract of Shioya, T. and Hirano, R. (1990) U.S. Patent No. 5,089,272 from American Chemical Society (1993).
Murphy, G.F., Orgill, D.P. and Yannas, I.V. (1990) Lab. Invest. 62, 305–313.
Slivka, S.R., Landeen, L.K., Zeigler, F., Michael, P. and Bartel, R.L. (1993) J. Invest. Dermatol. 100,40–46.
Muir, H. (1983) Biochem. Soc. Trans. 11,613–622.
Kjellén, L. and Lindahl, U. (1991) Ann. Rev. Biochem. 60, 443–475.
Garg, H.G. and Lyon, N.B. (1991) Adv. Carbohydrate Chem. Biochem. 49, 239–261.
Hay, E.D. (1981) J. Cell Biol. 91, (pt 2) 205s–223s.
Muir, H. and Hardingham, T.E. (1975) in Biochemistry of Carbohydrates, Biochemistry Series One, edited by W.J. Whelan, vol. 5, p. 153–222.
Wood, K.M., Wusteman, F.S. and Curtis, C.G. (1973) Biochem. J. 134, 1009–1013.
Hardingham, T. and Fosang, A. (1992) FASEB J. 6. 861–870.
Yanagishita, M. and Hascall, V.C. (1992) J. Biol. Chem. 267, 9451–9454.
Hirschman, A. And Dziewiatkowksi, D.D. (1966) Science, 154, 393–395.
White, D., Sandson, J., Rosenberg, L. and Schubert, M. (1963) J. Clin. Invest. 42,992–993.

(List continued on next page.)

Primary Examiner—Kathleen K. Fonda
(74) Attorney, Agent, or Firm—Frommer Lawrence & Haug; Thomas J. Kowalski; Grace L. Pan

(57) ABSTRACT

Non-immunogenic biocompatible macromolecular sheet composition are formed from a cellulosic membrane, a binding moiety having a plurality of functional groups, and a glycosaminoglycan (GAG). The binding moiety has the formula of $R^1$—X—$R^2$ wherein $R^1$ and $R^2$ are the same or different. The binding moiety, through functional groups binds the cellulosic membrane with the glycosaminoglycan. $R^1$ is covalently bound to a carbon or an oxygen of the cellulosic membrane. $R^2$ is covalently bound to a carbon, an oxygen, or a nitrogen of the glycosaminoglycan. The binding moiety can be bis-oxyrane, butanediol-diglycidyl ether (BDE), or divinyl sulfone. The cellulosic membrane can be a cellulosic membrane, partially acetylated cellulose and a copolymer of hydroxyethyl-methacrylate with methyl methacrylate, abbreviated as HEMA-MMA. The non-immunogenic biocompatible macromolecular sheet composition can be formed into a pouch to encapsulate cells, tissues, pharmaceuticals, or biological metabolic products. In addition, the non-immunogenic biocompatible macromolecular sheet composition can also be used as a skin graft or a skin substitute. Further, these non-immunogenic biocompatible macromolecular sheet composition can also be used as a surface to culture cells in vitro.

17 Claims, 5 Drawing Sheets

OTHER PUBLICATIONS

DiFerrante, N. (1964) Science, 143, 250–252.
Loewi, G. and Muir, H. (1965) Immunology 9, 119–127.
Boake, W.C. and Muir, H. (1955) The Lancet 269, 1222–1223.
Rodén, L., Baker, J.R., Cifonelli, J.A. and Matthews, M.B. (1972) Meth. Enzymol. 28, 73–140.
Carney, S.L. (1986) Proteoglycans, in Carbohydrate Analysis, a Practical Approach, edited by M.F. Chaplin and J.F. Kennedy, IRL Press, Washington, DC, Ch.4, p. 97–141.
Pearce, R.H., Mathieson, J.M. and Grimmer, B.J. (1968) Anal. Biochem. 24, 141–156.
Meyer, K. and Chaffee, E. (1941) J. Biol. Chem. 138, 491–499.
Berman, E.R. (1962) Biochim. Biophys. Acta 58, 120–122.
Yanagishita, M., Midura, R.J. and Hascall, V.C. (1987) Meth. Enzymol. 138, 279–289.
Bitter, T. and Muir, H.M. (1962) Anal. Biochem. 4, 330–334.
Dische, Z. (1947) J. Biol. Chem. 167, 189–198.
Davidson, E.A. (1966) Meth. Enzymol. 8, 52–60.
Brown, A.H. (1946) Arch. Biochem. 11, 269–278.
Gardais, A., Picard, J. and Tarasse, C. (1969) J. Chromat. 42, 396–407.
Dean, P.D.G., Johnson, W.S. and Middle, F.A. (1985), Activation Procedures, in Affinity Chromatography—a Practical Approach, Dean, Johnson and Middle, editors, IRL Press, Washington, DC, Ch.2, p. 31–59.
Glazer, A.N., Delange, R.J. and Sigman, D.S. (1975) Chemical Modification of Proteins–selected methods and analytical procedures, North Holland, Amsterdam, Ch.3, p. 99–101.
McPhie, P. (1971) Meth. Enzymol. 22, 23–32.
Schiller, S., Slover, G.A. and Dorfman, A. (1961) J. Biol. Chem. 236, 983–987.
Anderson, B, Hoffman, P. and Meyer, K. (1965) J. Biol. Chem. 240, 156–167.
Sajdera, S. and Hascall, V.C. (1969) J. Biol. Chem 244, 77–87.
Scouten, W.H. (1981) Affinity Chromatography: bioselective adsorption on inert matrices, John Wiley & Sons, New York, Ch.2 and 3, p. 20–84.

* cited by examiner

NON-IMMUNOGENIC, BIOCOMPATIBLE MACROMOLECULAR MEMBRANE COMPOSITIONS, AND METHODS FOR MAKING THEM

FIELD OF THE INVENTION

The present invention relates to non-immunogenic biocompatible macromolecular membrane compositions and methods for making and using the same. The non-immunogenic biocompatible macromolecular composition is preferably comprised of a membrane, more preferably, a cellulosic membrane, having bound, preferably covalently at, or on its surface to, one or more type of glycosaminoglycan, through one or more types of a binding moiety. The binding moiety preferably has a plurality of functional groups; more preferably, at least two functional groups, most preferably two functional groups. The cellulosic membrane is preferably covalently bound to one functional group of the binding moiety. The glycosaminoglycan (GAG) is preferably covalently bound to the other functional group of the binding moiety.

The invention therefore also relates to such selective membranes and methods of making and using them.

Certain documents are cited herein and, are incorporated herein by reference.

BACKGROUND OF THE INVENTION

A non-immunogenic biocompatible macromolecular molecular membrane composition is preferably substantially insoluble in bodily fluids, thus, non-biodegradable. Yet, it is also preferably suitable for contact with body fluids in or on the body. Ideally, such membrane composition has all or some of the following characteristics:

1. The membrane composition should avoid inducing undesirable reactions in the body (such as blood clotting, tissue death, tumor formation, allergy reaction, immune response or an inflammatory reaction).
2. The membrane composition should have desirable physical properties (such as strength, elasticity, permeability, and necessary flexibility).
3. The membrane composition should also be purified, fabricated, and sterilized easily.
4. The membrane composition should be able to maintain its physical properties and functions during the time the membrane composition remains implanted in or in contact with the host body.

While there are biocompatible macromolecular skin graft, or skin substitute compositions in the literature, an impediment for in vivo implantation (both cutaneously and in any degree more internal than cutaneous, e.g., subcutaneous or intraperitoneal application) of biocompatible implants is lack of reliability. Another deficiency of these implants is that they are often not retrievable after implantation. This deficiency is significant, particularly when combined with yet a further deficiency of these implants, namely that they can lose physical properties. For instance, implants made from biodegradable materials degrade over time and thereby induce a local or a systemic immune response in a host system. Further, another deficiency of implants is the difficulty to monitor and inspect such implants.

A number of approaches have been taken to improve the biocompatibility of implantable items. One approach was to prevent undesirable protein adhesion by providing a biomaterial with a low polarity surface, a negatively charged surface, or a surface coated with biological materials such as enzymes, endothelial cells, or proteins. Another approach was to coat solid surfaces with heparin, albumin, or streptokinase to enhance thromboresistance. However, these approaches have failed to teach or suggest the preferably covalent bonding of the present invention or the binding agent of the present invention, or the methods of making and using the invention including the pouch embodiments on structures.

Several researchers have proposed different approaches to protecting islet tissue from host attack after transplantation; these included encapsulation of islets in different materials such that insulin may be secreted but the beta-cells in the islet tissue will be immunologically isolated from the host. Polysaccharides have been proposed to form membranes, as is the case of agarose, by Howell, Ishaq and Tyhurst (Journal of Physiology 324, 20–21, 1982) or alginate, by Tze and Tai (Transplantation 33, 563–564, 1982). Search of the more recent literature indicates that the effort to develop new membrane materials for cell encapsulation for implants keeps a strong and steady pace. These include synthetic poly-acids and poly-bases (Bader et al., 1988 Eur. Pat. App. EP 280,155), gelatin and polyamino acids (Young et al., Biopharm 2, 34, 36, 38, 40–46, 1989) as well as different polysaccharides; chemically modified dextran, to form polyionically bonded capsules (Lim and Hall, 1988, PCT Int. Appl. WO 88 00, 327), entrapment in alginate followed by stabilization with poly-lysine and alginate (Chang and Wong, 1992, U.S. U.S. Pat. No. 5,084,350, as well as a combination of chitosan and carboxy-methyl cellulose to form capsules of controlled permeability (Shioyo and Hirano, 1990, U.S. Pat. No. 5,089,272). A recent review by Mikos et al. (Biotechnol. & Bioeng. 43, 673–677, 1994) discusses other alternatives, all with emphasis on synthetic materials as membrane components.

On the other hand, recent work bearing on regeneration of skin in culture has pointed out the important role of GAG's in the process, in studies where mixtures of collagen and GAG were used to support it (Murphy et al., Lab. Invest. 62, 305–313, 1990; Yannas et al., Polym. Mater. Sci. Eng. 62 801–803, 1990). Along the same line, but coming from another direction, keratinocytes and fibroblasts grown on a nylon mesh produced a dermal-like matrix containing heparan sulfate proteoglycans (Slivka et al., J. Invest. Dermatol. 100, 40–46, 1993).

These works, that show the importance of the extracellular matrix components in the normal development of the skin system, support the basis of our invention, that foreign membranes lined or structured with GAG's may constitute ideal materials for devices aiming at transplantation of cells or tissues of human or animal origin, with the purpose of treating or controlling disease. Their surfaces will contain critical elements for successful interaction with the host organism. Although GAG's occur in the organism mostly linked to proteins, as proteo-glycans, it has been demonstrated that the protein part only is immunogenic; the glycosaminoglycan component is not immunogenic by itself (Hirschmann and Dziewiatkowski, Science 154, 393–395, 1966; Loewi and Muir, Immunology 9, 119–127, 1965).

The extent of the interest in discovering the best way to use islets in transplantation is given by two recently published papers, one dealing with storage and preservation of islets (Jindal and Gray, Transplantation 57, 317–321, 1994) and the other with the action of prednisone on the islet autograft function (Rodrigues Rilo et al., Transplantation 57, 181–187, 1994). However, none of this work teaches or suggests the pouch system of the present invention where in cellulose macromolecular membrane is bound with GAG, formed into a pouch and cells are inserted into it.

Likewise, species within the term glycosaminoglycan ("GAG") may have been mentioned in connection with compositions, but these compositions are unlike the present invention, and, so too are the prior approaches to improve biocompatibility.

For instance, Guire, U.S. Pat. Nos. 4,979,959 and 5,263,992, relate to materials having a surface coating which is a covalently bound biocompatible agent. While cellulose is included in a long list of allegedly possible materials and heparin is included in a long list of allegedly possible agents, there is no teaching or suggestion to specifically select the combination of cellulose and heparin or, any working example thereof. Further, Guire's reagents require activation by light in order for the reaction to proceed. A "dark room" type of reaction with subsequent light activation is thus required; and, this is complicated and presents economic deficiencies and industrial scale-up or other preparation or utility problems. In contrast, the present invention specifically calls for a cellulose membrane having glycosaminoglycan covalently surface bound via a linker molecule, a binding agent bound without any need for light activation. For instance, conditions of pH and temperature may be favorable for binding, without resort to any complicated photoreaction. Consequently, Guire, either individually or in any combination, contains no teaching or suggestion of the present invention or, of the pouch embodiments or methods of the invention.

Tsilibary, U.S. Pat. No. 5,152,784, is directed to a polypeptide which represents a fragment of the α 1 chain of type IV collagen which is a promoter for binding heparin to synthetic substrates in order to facilitate cellular adhesion or growth surface. However, Tsilibary's polypeptide contains a glycoprotein which has been demonstrated as a source for eliciting an immune response. Thus, Tsilibary is contrary to, and, either individually or in any combination, fails to teach or suggest the present invention. See, Hirschman and Dziewiatkowski, Science 154, 393–395, 1966; Loewi and Muir, Immunology 9, 119–127, 1965. Further, macromolecular structures and uses therefor as herein taught are not disclosed or suggested in Tsilibary.

Lim, U.S. Pat. No. 4,409,331, relates to a method of using polysaccharides to encapsulate islet cells which secrete insulin. However, there is no teaching or suggestion in Lim of macromolecular structures or, of the binding agent or linker molecule in the present invention. Further, Lim does not teach or suggest encapsulating cells nutrient or anything else for secretion in vivo or in vitro or use growing media or as a pouch. And therefore, Lim, either individually or in any combination fails to teach or suggest the present invention.

Yannas, et. al., U.S. Pat. No. 4,060,081, is directed to a two-layer membrane for use as a synthetic skin. The first layer is formed from crosslinking composites of collagen and a mucopolysaccharide and the second layer is formed from a nontoxic synthetic polymers such as silicone resins, polyacrylate, or polymethacrylate esters or their copolymers, and polyurethane. The present invention does not involve crosslinked composites of collagen or of glycosaminoglycan. Brazilian Patent No. 38404937 relates to a cellulose pellicle for treating skin injuries but, the pellicle does not have GAG bound at or to its surface. Accordingly, Yannas and Brazilian Patent No. 38404937, either individually or in any combination, fails to teach or suggest a non-immunogenic macromolecular cellulosic membrane having GAG covalently bound thereto through a linker molecule. As in the present invention, or the structures or embodiments thereof and uses therefor of the present invention.

Meisner, et. al, U.S. Pat. No. 4,585,754, relates to orally administering insulin formed from reacting it with chondroitin or, more generally to stabilizing a pharmaceutically active substance to produce an ester and/or amide derivative thereof. Nimni, et al., U.S. Pat. No. 4,378,224, relates to crosslinking a GAG (not necessarily preferred in the present invention, see infra) and covalently binding it to an allograft or heterograft. Barbucci, et al., U.S. Pat. No. 4,944,767 relates to synthetic material apt to stably absorb high quantities of heparin. However, there is no teaching nor suggestion in Meisner, Nimni, or Barbucci of any biocompatible macromolecular membrane composition or of the binding agent or linker molecule or uses and embodiments or structures of the composition of the present invention; and therefore these documents, either individually or in any combination fail to teach or suggest the present invention.

Rase, et. al, U.S. Pat. No. 5,169,631, relates to a topical antimicrobial composition containing an antimicrobial agent wherein the wall of the microcapsule is formed from cross-linking collagen and a GAG by a cross-linking agent. Yannas, et al., U.S. Pat. No. 4,955,893, is directed to biodegradable polymers of uncrosslinked or crosslinked collagen-GAG. Collombel, et al., U.S. Pat. No. 5,166,187, relates to a material having a base mixture of collagen, acetylated chitosan, and a GAG. Noishiki, et al., U.S. Pat. No. 4,704,131, relates to a material containing heparinized collagen bound to a GAG. There is no teaching or suggestion in Rase, Yannas, Collombel, or Noishiki of any biocompatible macromolecular membrane composition or of the binding agent or composition structures and uses of the present invention; and therefore, these documents, either individually or in any combination fail to teach or suggest the present invention.

Huc, et al., U.S. Pat. No. 5,071,436, relates to a collagen hydroxy-apatite bound to a GAG composition. Stone, U.S. Pat. Nos. 5,108,438, 5,116,374, and 5,258,043 is directed to a meniscus which has dry, porous, volume matrices of fibers wherein GAG can be interspersed in the fibers for crosslinking. There is no teaching nor suggestion in Huc or Stone of any biocompatible macromolecular membrane composition, or of the binding agent or composition structures or uses of the present invention; and therefore, these documents, either individually or in any combination, fail to teach or suggest the present invention.

Chu, et al., U.S. Pat. No. 5,024,841, relates to a collagen implant formed from collagen fibrils. Benitz, et al., U.S. Pat. No. 4,945,086, relates to an epithelium-derived inhibitor of the growth of smooth muscle cells, along with methods for purifying such substance. As initially isolated, the inhibitor can be a heparin sulfate proteoglycan which releases a GAG chain on protease cleavage. Gallo, et al., U.S. Pat. No. 5,129,877, relates to a delivery system for biologically active materials consisting of polysaccharide or polypeptide microspheres which bind to a GAG receptors on cell surfaces. There is no teaching nor suggestion in Chu, Benitz, or Gallo of any macromolecular membrane composition, or of the binding agent or composition structures or uses of the present invention; and therefore, these documents, either individually or in any combination fail to teach or suggest the present invention.

Cristofori, et al., U.S. Pat. No. 5,252,339, relates to an oral pharmaceutical composition coated by an enterosoluble gastroresistant film containing a lyophilizate consisting of therapeutically effective amounts of a GAG, a thickening substance and surfactants and process for obtaining them. Huc, et al., U.S. Pat. No. 5,244,672, is directed to a composition containing liposomes which is stabilized by a stabilizing support comprising a mixture of atelocollagen and a GAG. However, there is no teaching nor suggestion in Cristofori or Huc of the macromolecular membrane composition, or the binding agent of the present invention; and therefore, these documents, either individually or in any combination fail to teach or suggest the present invention.

It can therefore be appreciated that there is a long-felt need for a non-immunogenic, biocompatible macromolecular membrane composition, particularly of such a composition in which the membrane is a cellulose membrane to which GAG is covalently surface bound through a linker agent, especially such a membrane composition in the form of a pouch containing an active ingredient such that molecules selectively pass into and out of the pouch; and, that there is a long-felt need for methods of making and using such a membrane.

Indeed, not only for implantation (cutaneous or any degree subcutaneously) or any in vivo setting, but also for in vitro and ex vivo applications there has been a long-felt need for the present invention and methods thereof. For instance, in vitro cell culturing for either harvesting cell product or harvesting the cells themselves, for instance for readministration (ex vivo), or simply harvesting using conventional media, dishes or broths presents a plethora of avenues by which non-biocompatible or immunogenic molecules or contaminants may be introduced to the cells or any harvest therefrom. Such cells can be antibody-producing cells for harvesting binding molecules, e.g., antibodies or cells such as post-stimulated or antigen-exposed cells, or cells which produce a needed biomolecule such as a hormone, e.g., insulin, i.e., islet of Langerhans cells. By either culturing over or within a preferably cellulosic selective membrane pouch to which glycosaminoglycan is bound, as in the present invention, such deficiencies of conventional dishes, media and broth are diminished.

Also, mention is made that cross-linked compositions in the literature provide for a rigid membrane. Non-cross linkage, for instance, in preferred embodiments in the present invention, provide a significant departure from that which has not been heretofore, for instance, a flexible membrane such as a pouch, suitable for implantation or other use in vitro in virtually unlimited locations.

OBJECTS AND SUMMARY THE INVENTION

It is an object of the invention to provide a non-immunogenic, biocompatible macromolecular membrane composition and methods of making and using such.

It is also an object of the invention to provide such a composition having a cellulose membrane as the membrane and immunogenic, biocompatible properties by virtue of GAG covalently bound at or to the surface of the membrane via a binding agent having at least two or a plurality of functional groups.

It is yet an object of the invention to provide such a composition in the form of a sheet.

It is another object of the invention to provide such a composition in the form of a pouch.

It is additionally an object of the invention to provide a surface or a space, such as on the exterior or within a composition either in sheet or pouch form for culturing cells, harvesting product therefrom or otherwise delivering, administering or secreting a substance in vitro or in vivo as well as to provide methods employing such.

It is still further an object of the present invention to encapsulate islet of Langerhans cells in a pouch of the invention so that these cells can produce insulin in in vivo or in vitro.

It is yet further an object of the invention to provide a method of treating diabetes mellitus, such as Type I, by implanting such an islet cell pouch in an individual in need of such treatment or, of producing insulin in vitro by culturing such cells within or on the exterior of the pouch and harvesting the insulin either on the exterior or interior of the pouch, with optional washing.

It is still another object of the invention to provide an implant or transplant system which exhibits a suitable level of biophysical stability or biocompatible devices after implantation or transplant.

It is yet another object of the present invention to provide a composition exhibiting suitable longevity and/or flexibility for instance, for use in transplant, implant, biocompatible device, or culturing or harvesting.

It is yet a further object of the present invention to substantially avoid an elicited immune response by an antigen or immunogen by encapsulating either cells or product therefrom in a biocompatible macromolecular membrane composition.

It is also an object of the present invention to provide a biocompatible encapsulating system, such as a biocompatible macromolecular membrane composition in pouch form, that can anchor itself or be anchored in a host organism or, to provide an anchor means for encapsulated implanted cells, for anchoring them within an encapsulating system or within a host.

It is additionally an object of the invention to provide an in vivo system capable of controlling or treating or preventing a medical condition in an individual in need thereof by secretion or administration by osmotic or other relative concentration driven mechanism of a substance for such control or treatment or prevention from secretion by implanted cells expressing the substance or from the substance encapsulated in a permeable, enclosed, membrane system that is preferably non-immunogenic and/or biocompatible.

It is yet additionally an object of the invention that such substance crosses the membrane, enters into the system, e.g., circulatory system of the host and/or then is distributed to target cells or organs.

It is yet another object of the invention to provide a macro-envelope encapsulation system that has resistance to biodegradation caused by enzymes or cells from the host in which the system is implanted, thereby preventing the contents of the envelope from being exposed to the host's systems or cells, thus averting an occurrence of a systemic immune response with eventual destruction of the system implanted and leaving behind an immune sensitivity to a future implant of the same type.

The present invention therefore provides a non-immunogenic biocompatible macromolecular composition preferably comprised of a cellulosic membrane covalently having bound at or on its surface to glycosaminoglycan through a binding moiety. The binding moiety is a compound of a general formula of $R^1$—X—$R^2$ wherein $R^1$ and $R^2$ independently of each other is a moiety which bonds to GAG and membrane by forming a bond with an oxygen or carbon of each or with a nitrogen of GAG; for instance, the bond can be an ether, ester, carbamate, or amide bond. $R^1$ and $R^2$ independently of each other can be a $C_2$–$C_6$ alkylene, a $C_2$–$C_6$ heterocycle wherein there is 1 to 2 hetero atoms which can be oxygen or nitrogen (e.g., oxyrane, epoxide), $C_1$–$C_6$ dinitride, cyanogen halide (e.g., ClCN, BrCN, ICN, FCN), cyanuric halide (e.g., cyanuric chloride such as trichloro S-triazine), halide substituted pyrimidine, such as 2,4,6-trifluoro-5-chloropyrimidine, N,N'-dicarbamiate such as N,N'-disuccinimdyl-carbamate, or an imidazolyl such as carbonyl di-imidazole; X can be a $C_1$–$C_6$ alkane, a $C_2$–$C_6$ alkylene, sulfone, —$SO_2$— or an aromatic or heterocycle such as a $C_3$–$C_8$, preferably $C_6$ aromatic or $C_2$–$C_6$ heterocycle with 1 or 2 hetero atoms or an aromatic heterocycle with 1 or 2 hetero atoms such as S-triazine or pyrimidine. $R^1$—x—$R^2$ can be an activated carbonyl such as carbonyl di-imidazole or can be a disubstituted carbodiimide such as 1-ethyl-3-(3-dimethylaminopropyl)-carbodiimide.

The composition can be in the form of a sheet or a pouch formed from a sheet.

The composition acts as a membrane. The pore size is preferably permeable to molecules or ions of less than about 100,000 daltons.

In the pouch from the composition comprises two sheets of the composition adhered at the periphery, in face-to-face relationship or, one folded sheet adhered at the periphery, in face-to-face relationship, with means defining a hollow space within the pouch. That is, the interior of the pouch is hollow for containing anything desired to be within a biocompatible, non-immunogenic membrane pouch, for instance, cells, tissues, pharmaceuticals, medicinals, including immunologicals, and metabolic products, vaccines, inhibitory or treatment preparations or biological products. Thus, the invention provides pouch compositions with cells, nutrients, or any other biomolecules within or on the exterior of the pouch, and to methods of making an using the same.

For instance, the invention provides a pouch of the composition with cells within the pouch and nutrient therein or absorbed therethrough with cell products harvested from passing out of the pouch either before or after washing any excess nutrient, if present, from pouch surface, either in vitro or in vivo; or, a pouch with nutrient within the pouch and cells grown thereon with product harvested from the cells; or, a pouch with cells grown on the pouch with nutrient added thereto with neither the cells nor nutrient readily passing into the pouch, with interior of pouch preferably also having GAG bound thereto (preferably covalently), and cell product passing into and harvested from the pouch interior, preferably after washing away cells and nutrient from pouch exterior; or, to a pouch with a pharmaceutical or other preparation to be administered within the pouch for gradual or otherwise secretion (passing through the membrane) either in vitro or in vivo.

Accordingly, the invention provides selective membrane compositions, e.g., molecules of certain weight or size pass therethrough whereas other, preferably immunogenic molecules do not (for instance, neither into or out of the pouch); and, the invention therefore also provides methods of making and using them. The pore size is preferably such which, in certain embodiments, prevents antibodies and antibody producing cells, e.g. lymphocytes, from entering the pouch.

The composition of the invention can also be used as a skin graft or substitute or as a bandage or dressing or as a means to adhere to living cells or tissue (since GAGs may bond to cells). Accordingly, the invention also provides a skin graft or substitute or a dressing or bandage or as adhesive material for adhering to living cells or tissue and methods employing the same. For instance, methods of grafting or substituting skin or dressing or bandaging a wound comprising applying a composition of the invention to an individual in need of such.

This invention is essentially unlimited to the types of cells that may be encapsulated in a pouch. Cultures of cells from the tissue of higher animals as well as microorganisms may be employed. For instance, the cells can be islet of Langerhans cells and insulin secreted therefrom and from the pouch either in vitro or in vivo, for harvesting insulin or, for implantation for treatment of diabetes for those in need of such treatments.

The practice of the non-immunogenic biocompatible macromolecular composition has at least a dual advantage. The non-immunogenic biocompatible macromolecular composition in pouch form can be used as a vehicle to provide a protective environment for the implanted cells which are capable of producing biometabolic products, which products are then released into the host circulatory system, while, in the meantime, the pouch allows these implanted cells to draw nutrients from the host system.

Other objects and embodiments are disclosed or are apparent from the following detailed description.

BRIEF DESCRIPTION OF DRAWINGS

In the following detailed description reference will be made to the accompanying drawings wherein.

DETAILED DESCRIPTION OF THE INVENTION

Figure 1:
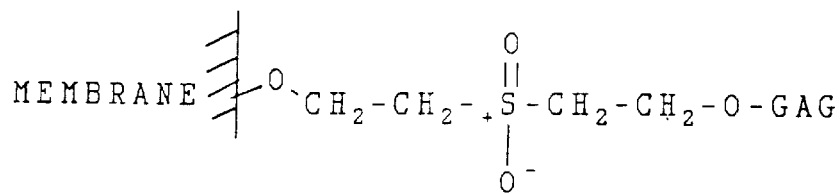
FIG. 1 shows a cellulosic membrane covalently bound to the binding moiety, divinyl sulfone, and the moiety also bound to GAG with the bonds being ether bonds.

Contrary to the already existing technology, the present invention uses covalent linkage to provide the membrane with a flexible characteristic, thus prevent the hardening of the device after prolonged implantation.

The present invention relates to a non-immunogenic biocompatible macromolecular composition and its preparation and use. A membrane composition is characterized as "biocompatible" if is capable of functioning and/or existing in contact with biological fluid and/or tissue of a living organism with a net beneficial effect without eliciting an immune response in the living organism. Long term biocompatibility is desired for the purpose of reducing disturbance to the host organism if used in vivo, as well as to provide products over a period of time when used In vitro. In the present invention, GAG, a non-immunogenic polysaccharide without protein, is used to make the macromolecular composition biocompatible.

This biocompatible macromolecular composition is capable of encapsulating cells, tissues, pharmaceuticals, biological metabolic products, or be used as a skin graft or a skin substitute. The composition is permeable and preferably has an upper limit of permeability sufficient to allow traverse of ions, amino acids, and other cell nutrients while keeping out host antibodies and immunogens. More specifically, the present invention relates to a non-immunogenic biocompatible macromolecular composition comprising a cellulosic membrane, a glycosaminoglycan (GAG) and a binding moiety having a plurality of functional groups.

Glycosaminoglycan (GAG) is selected as an agent to provide biocompatibility to the membranes in the composition of present invention because GAGs are non-immunogenic. They do not elicit an immune response from the host even if injected into the blood stream. Another advantage of using GAGs is that they are ubiquitous components of the extracellular matrix. GAGs are capable of performing functions such as structural control of diffusion and permeability of solutes, specific cell adhesion, and mechanical resistance. Although one would be able to bind GAG directly to a cellulosic membrane by a dehydrothermal crosslinking such as disclosed in Yannas, double bonds ($>C=\!\!=\!\!C<$) that may be formed by this dehydrothermal crosslinking would evoke antibodies against the membrane, thus causing an immune response.

GAGs that are suitable for the present invention include chondroitin-4-sulfate, chondroitin-6-sulfate, dermatan sulfate, keratin-sulfate, hyaluronic acid, heparin sulfate, and heparin. (Structural formulae of the repeating disaccharide units of some major glycosaminoglycans are hereby incorporated by reference. Lubert Stryer, Biochemistry, 1981, at 201 (1981)).

The binding moieties that are suitable for the invention are most preferably selected from the group consisting of carbonyl di-imidazole, a substituted carbodiimide such as 1-ethyl-3-(3-dimethylaminopropyl)-carbodiimide. In addition, the binding moiety of the present invention provides a means for spacer arms to separate the cellulosic membrane from the GAG.

Preferably, divinyl sulfone and butanediol-diglycidyl ether (BDE) are the binding moieties as described in Examples 1 and 2. These binding moieties are commercially available from Sigma Chemical Company of St. Louis, Mo.

The binding moiety has a general formula of $R^1$—X—$R^2$ wherein $R^1$ and $R^2$ independently of each other is a moiety which binds to GAG and membrane by forming a bond with an oxygen or carbon of each or with an oxygen or a nitrogen of GAG; for instance, the bond can be an ether, ester, carbamate, or amide bond. $R^1$ and $R^2$ independently of each other can be a $C_2$–$C_6$ alkylene, a $C_2$–$C_6$ heterocycle wherein there is 1 to 2 hetero atoms which can be oxygen or nitrogen (e.g., oxyrane, epoxide), $C_1$–$C_6$ dinitride, cyanogen halide (e.g., ClCN, BrCN, ICN, FCN), cyanuric halide (e.g., cyanuric chloride such as trichloro Striazine), halide substituted pyrimidine, such as 2,4,6-trifluoro-5-chloropyrimidine, N,N'-dicarbamate such as N,N'-disuccinimdyl-carbamate, or an imidazolyl such as carbonyldiimidazole; X can be a $C_1$–$C_6$ alkane, a $C_2$–$C_6$ alkylene, sulfone, —$SO_2$— or an aromatic or heterocycle such as a $C_3$–$C_8$, preferably $C_6$ aromatic or $C_2$–$C_6$ heterocycle with 1 or 2 hetero atoms or an aromatic heterocycle with 1 or 2 heteroatoms such as S-triazine or pyrimidine. $R^1$—X—$R^2$ can be an activated carbonyl such as carbonyl di-imidazole or can be a disubstituted cabodiimide such as 1-ethyl-3-(3-d'methylaminopropyl)-carbodimide. Compounds $R^1$—X—$R^2$ are known in the art and can be prepared by employing knowledge in the art or, they are commercially available.

Both the cellulosic membrane and the GAG form stable covalent bonds to both $R^1$ and $R^2$. $R^1$ and $R^2$ are sufficiently reactive at temperatures not far from the ambient or room temperature. For instance, the reaction to link the binding moiety to GAG can be at 0° to 100° C., preferably between 4° C. and 60° C. more preferably between 20° to 40° C. Further, the chemical bonds formed between the cellulosic membrane and the binding moiety and the GAG and the binding moiety are stable in hydrolysis. In addition, $R^1$ and $R^2$ react more favorably to chemicals having hydroxyl groups and primary amino groups, as they exist in the cellulosic membrane and the GAG. Chemical reactions of such nature are set forth in the Examples. Further, the resulting products from these chemical reactions are not antibody-eliciting since a cellulosic membrane and a GAG stripped of proteoglycans are non-immunogenic.

Purified GAGs are commercially available and can be readily purchased from Sigma Chemical Company, or be prepared by procedures published in "Proteoglycans" by N. S. Pedarko, edited by P. Jollès, Birkhäuser Verlag, Basel, Pages 9–35, 1994. In its natural state, GAG is linked to protein, such as proteoglycan. It has been demonstrated that only the protein part of the GAG is immunogenic and that the GAG component by itself is not immunogenic. Hirshmann and Dziewiatkowski, Science 154, 393–395, 1966; Loewi and Muir, Immunology 9, 119–127, 1965. The isolation of the several types of GAGs using dissociative methods is preferentially used in association with detergent and ethanol precipitation, as well as ion-exchange chromatography on DEAE-Sephadex resins. Purification indices as well as characterization of the fractions obtained is done by chemical determination of the reference monomers, as is the case for glucuronic and iduronic acids, hexosamines, and reducing sugar. Ion-exchange chromatography is used to separate the major components. Molecular weight of the GAG polymers is determined by viscosity, electrophoresis, and gel permeation. Isolation, purification, ion-exchange and molecular weight determination can all be done by techniques known in the art.

The protein portion is split off the proteoglycan structure by alkaline hydrolysis or by proteolysis, or both. GAGs obtained by this process with or without at least one amino acid residue attached to the reducing end of the polysaccharide chain, respectively, are used in the present invention.

The covalent attachment between the cellulosic membrane and the binding moiety as well as between the GAG and the binding moiety form flexible "arms". The chemical construction of the covalent attachment is such that the GAG molecules attached to the cellulosic membrane have a degree of freedom to rotate or to Rove on and about the membrane surface, since there is a distance between the cellulosic membrane and the GAG, allowed for by the size of the binding moiety, which is comparable to an "arms length". The length, of course, is not such that would cause the binding moiety to bind on both ends to the GAG or to the membrane. That is, each of $R^1$, X and $R^2$ are chosen so that their size does not allow for excessive or in some cases any bonding by both ends to either the membrane alone or GAG alone.

More specifically, as illustrated in FIGS. 5–10 and described below, the binding moiety is first bound to one or the other of the membrane and GAG, i.e., either the membrane (and preferably the membrane) or the GAG is "activated" by having bound to its surface the binding moiety and then the other of either the GAG (and preferably the GAG) or the membrane is bound to that which has been activated. The binding moiety is not so long or it has a size (hindrance) that its ends both bind to the membrane or the GAG, thereby not obtaining an activated membrane or GAG.

The chemical bonds between the binding moiety and each of the GAG and membrane are no stranger to the chemistry of living beings, nor do they elicit any kind of immune response. In addition, these new bonds are stable within living organisms. The bonds formed between the cellulosic membrane, GAG, and the binding moiety can be an ether bond, an ester bond, a carbamate bond, or an amide bond. $R^1$ or $R^2$ is covalently bound to a carbon, or an oxygen of the cellulosic membrane. $R^1$ or $R^2$ is covalently bound to a carbon, an oxygen, or a nitrogen of the GAG.

Figure 2:
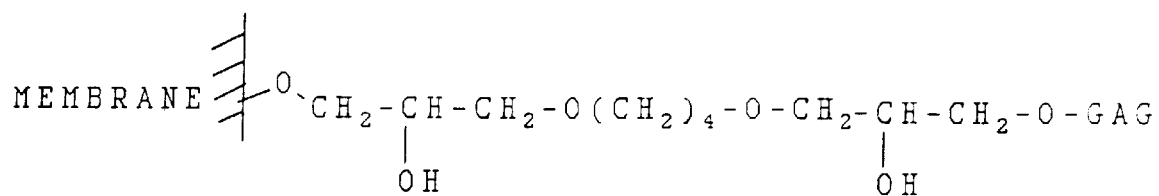
FIG. 2 shows a cellulosic membrane covalently bound to the binding moiety, a di-epoxide or a bis-oxyrane, 1,4-butanediol-di-glycidyl ether, and the moiety also bound to GAG with the bond being ether bonds.
Figure 3:
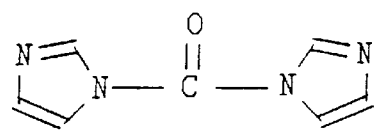
FIG. 3 shows the chemical structure of an activated carbonyl such as carbonyl di-imidazole.

As to the reaction, with reference to FIGS. 1 to 10, preferably the membrane is "activated" by reacting it with the binding moiety. For instance, using suitable reaction conditions, the hydroxy groups of the membrane are first reacted with a functional group of the binding moiety, e.g., EDC, BrCN, FCP, DSC, glycidol, trichichloro-5-triazine (FIGS. 5 to 10). The membrane, after this first reaction, is "activated". That is, the membrane has bound to it the binding moiety with an exposed functional group which is reactive with GAG. In a second reaction, under suitable conditions, the activated membrane is reacted with GAG so that through the binding moiety GAG is bound to the membrane. Suitable membrane compositions are illustrated as end-products in FIGS. 5–10, as well as in FIGS. 1, 2 and 4. A suitable binding moiety, an activated carbonyl is shown in FIG. 3. Reaction conditions for the reaction of the binding moiety to the membrane and for the activated membrane to GAG can be determined by the skilled artisan from the knowledge in the art of organic chemistry and, from this disclosure, without undue experimentation.

The biocompatible macromolecular composition of the present invention has a variety of utilities.

The non-immunogenic biocompatible macromolecular membrane composition can preferably be used for encapsulating cells, tissues, pharmaceuticals or medicinals, including immunologicals, and metabolic products, vaccines, inhibitory or treatment preparations or biological products; or, used as media or as a skin graft, a skin substitute; or, used as a surface for culturing cells in vitro.

The invention thus can be used in the form of a pouch with cells, nutrients, or any other biomolecules within or on the exterior of the pouch, and to methods of making and using the same; for instance, cells can be within the pouch and nutrient therein or absorbed therethrough with cell products harvested from passing out of the pouch either before or after washing any excess nutrient, if present, from pouch surface, either in vitro or in vivo; or, nutrient within the pouch and cells grown thereon with product harvested from the cells; or, cells grown on the pouch with nutrient added thereto with neither the cells nor nutrient readily passing into the pouch, with interior of pouch preferably also having GAG bound thereto (preferably covalently), and cell product passing into and harvested from the pouch interior, preferably after washing away cells and nutrient from pouch exterior; or, a pharmaceutical or other preparation to be administered within the pouch for gradual or otherwise secretion (passing through the membrane) either in vitro or in vivo.

Accordingly, the membrane composition of the invention is also useful as a selective membrane, e.g., molecules of certain weight or size pass therethrough whereas other, preferably immunogenic molecules do not (for instance, neither into or out of the pouch).

The cells and tissues encapsulated may be obtained by immobilization and immunoisolation by three basic techniques known to those skilled in the art. These techniques are: in extravascular, in spherical dispersions or microcapsule, and within macrocapsules, in the form of sheaths, rods or disks. Using any one of these techniques, a great variety of cells and tissues of different animals have been immunoisolated, encapsulated, and implanted in animals for development of therapeutic systems.

Indeed, applications of immunoisolated cell therapy includes therapy for diseases or conditions such as diabetes, hemophilia, hepatic failure, Alzheimer's, Parkinson's and Huntington's diseases, affective disorders, hepatic failure and fertility problems. Thus, the invention comprehends pouches containing suitable cells which secrete suitable compound for treatment of these diseases or conditions, which are then useful for in vivo implantation or in vitro isolation through the pouch of the suitable compound as well as to treatment methods employing filled pouch.

Currently available treatment for Type I diabetes includes pancreas transplant, insulin pump that delivers insulin under a controlled program, and more recently, Langerhans' islets transplantation became available. However, recent studies indicate difficulties in protecting these implanted islet cells from host attack after transplantation. These studies encompass encapsulation of islet cells in different membrane materials in order to allow insulin secreted to pass through the membrane materials while keeping the beta-cells in the islet tissue immunologically isolated from the host. In the case of diabetes mellitus, safer and more convenient alternatives to daily insulin injections have been since long desired. A review of sustained-release implants for insulin delivery has been published (Wang, 1991).

Consequently, there is a recognized long-felt need to improve treatment by utilizing a non-immunogenic biocompatible implantation system which renders the treatment more durable, yet minimizing negative host response, such as an immune response.

It has now been found that membranes containing polar groups, such as cellulosic membranes, may be reacted with complex polysaccharides of the GAG type, GAG, through stable, covalent bonds, thereby becoming reinforced in structure and acquiring new properties in relation to their use as macro-encapsulation devices for the transplant or implant of cells or tissues into humans, with the purpose of treating or preventing disease. At least in one case, cellulosic membranes, as sheets, can also be used directly to protect injured skin surfaces during recovery and healing (Farah, L. F. X., BR 8,404,937; Ring et al., U.S. Pat. No. 4,788,146).

As a constituent of the extracellular matrix in connective tissues, of cell membrane and endothelial lining, the overall presence of GAG clearly indicates its importance in matrix formation, its extension both in cell-matrix or cell-cell interactions, and in a normal development of the skin system can be inferred. Use of GAG in the present invention is ideal since it is non-immunogenic. Consequently, the membrane composition of the present invention having GAG bound to its surface provides the necessary elements to successfully interact and bind with host organisms. Further, the membrane composition of the invention having GAG bound to its surface is ideal material for encapsulating and transplanting cells or tissues of human or animal origins. The implant or the transplant of the present invention inhibits calcification, platelet aggregations, fibrin depositions, anaphylactic responses, enzymatic degradations, aneurysm formations, host rejections, and minimizes the risk of mechanical failure in the host organism.

The macroencapsulation herein described of this invention can be used to implant animal cells, mammalian cells, even bacterial cells into humans or animals with the following advantages:

1. The macrocapsules, envelopes, or pouches can be retrieved easily with full recovery of the implant including the transplanted cells or tissues.
2. The cells contained therein are fully immunoisolated from the host.
3. Substantially, only metabolites secreted or other cell expression products by the implanted cells such as insulin, e.g., islet cells, can cross the macrocapsule membrane barrier and enter into the host system since the membrane thus made has a pore size of about less than 100,000 daltons and nutrients desired by these implanted cells. This pore size of the present invention can also keep out of the pouch most of the larger molecules such as immunoglobulins produced by the host.
4. The implant may be used as an acute phase therapeutic agent, to be retrieved later on, or as a chronic therapeutic agent, as would be the case in the management of diabetic patients.
5. The membranes (pouches) thus designed minimize irritability and immune response by the host animal.

Membranes other than cellulosic membrane can be employed in the invention, provided that these membranes have functional groups capable of forming covalent bonds with an activating reagent and that their pore sizes are adjustable by chemical modification. In addition, these membranes preferably elicit minimal inflammatory responses when implanted in a host system.

Other materials that can used to form the non-immunogenic biocompatible macromolecular composition include partially acetylated cellulose and a copolymer of hydroxyethyl-methacrylate with methyl methacrylate, abbreviated HEMA-MMA. Preferably, cellulosic membranes are most ideal and they are formed from fermentation of Acetobacter bacteria. These membranes are commercially available and may be obtained from Biofill-Biological Products S.A., in Curitiba, Paraná state in Brazil.

Figure 11:
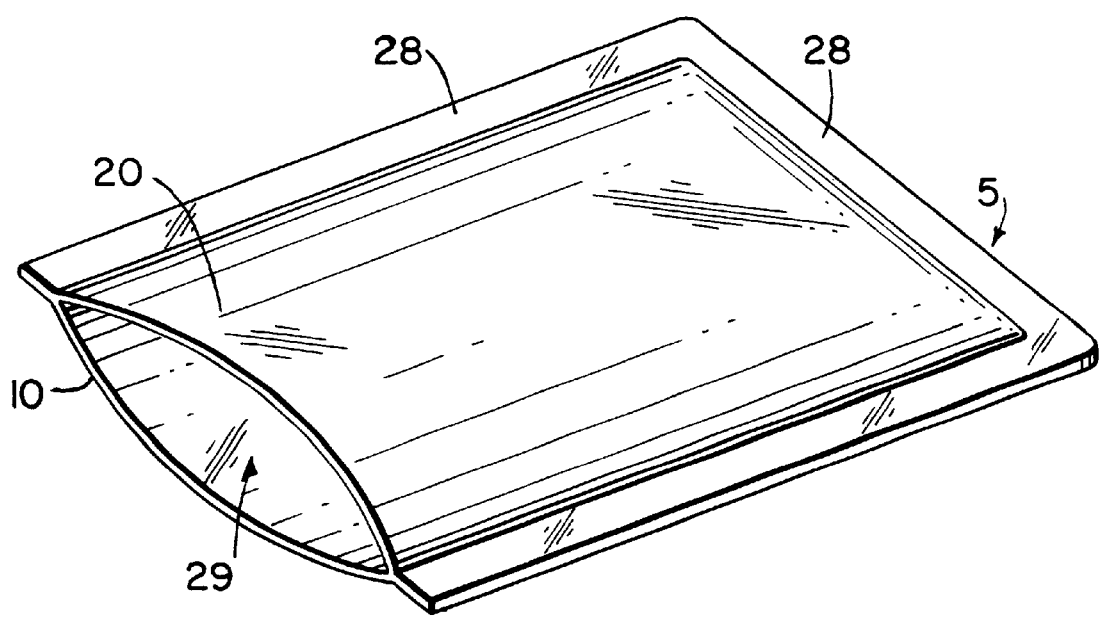
FIG. 11 shows a composition of the invention in the form of a pouch.

The membrane composition of the invention is selectively permeable as to molecular sizes. The membranes can also be made into an envelope or a pouch as shown in FIG. 11. Sheets 10 and 20 of pouch 5 are made by bonding GAG to cellulose membrane via a binding moiety, as discussed above. By using an adhesive such as silicone medical Adhesive A, cyano acrylates, or any other suitable adhesives, sheet 10 is adhered to sheet 10 along the periphery 28. As shown three sides are sealed at periphery 28, with the fourth side having opening 29. Contents for placing within the pouch can be introduced into the pouch via opening 29 and, the fourth side then sealed. Alternatively, one sheet can be folded to have a top portion 20 and a bottom portion 10 with seals 28 placed about three sides of the periphery and then leaving the fourth side as open end 29. Also, all side can be sealed either by folding one sheet or by placing two sheets in face-to-face arrangement, and, as alluded to above, contents for the pouch injected into the pouch, providing that the injection does not introduce a pore which is too great in size. The manufacture of pouches of the invention can be automated, as in the packaging industry. For instance, the membrane composition of the invention in sheet form can be made into pouches by means of a modified form, fill and seal apparatus. For instance, the sheet can be formed into a tube with an adhesive seal along opposing edges and, transverse seal(s) formed along the width of the tube by means of adhesive.

Once inserted in the body, the biocompatible macromolecular membrane composition (pouch) can isolate and protect the donor cells or tissues encapsulated within the membrane composition (pouch) form host immunoglobulin. The amount of cells in the pouch is preferably about 100,000 to 1.5 million cells, more preferably no less than 300,000 cells, and most preferably about 300,000 to about 1 million cells, suspended in a solution about 2 to 4 milliliters in each of the macroenvelope. For a background on the subject of islet numbers a paper authored by Ricordi et al., biabetes 37 413–420, 1988 is recommended. These macro-envelopes are preferably implanted subcutaneously in locations not subject to strong mechanical forces or stresses. These locations include but are not limited to abdomen, flank, chest, or back. Subcutaneous implantation is preferred since it allows for a light surgical procedure, is easy to monitor by visual inspection, and renders recovery or substitution of the implant easily accessible. However, subcutaneous implantation for Langerhans Islets is less preferable since there is an inadequate supply of blood available beneath the skin. The deficiency in blood supply hinders the implanted cells from receiving adequate nutrients and impairs an efficiency transportation of the secreted insulin. Although an intraperitoneal implantation can be exploited to overcome the deficiency presented by subcutaneous implantation, the intraperitoneal procedure involves a higher risk. Thus, it is not an alternative without consequences.

However, the amount of cells and location for implantation may be varied by the skilled artisan, without undue experimentation from this disclosure taking into account typical factors, such as age, weight, sex, and condition of patient.

These membrane compositions in pouch form can also be used to enclose devices such as electrodes, which can be used to perform continuous monitoring of the human body, such as blood to ascertain glucose level. Consequently, the membrane compositions or pouches can protect medical devices from being corroded or attacked by the host organism. Still further, the membrane compositions can be used to envelope larger tissue preparations for implantation, such as liver cells or others, granting temporary function of essential mechanisms in the body. Of course, from this disclosure, the skilled artisan can, without undue experimentation determine the amount of cells and location for implantation taking into account typical factors.

The applications of the membrane compositions are, therefore, ample and they are easily understood by those who are skilled in the art of cell or tissue transplantation.

The nature of the attachment reaction of the membrane composition is such that it takes advantage of the chemical composition of GAG. GAG molecules can be combined in a given membrane preparation in order to mimic any desired specific host tissue composition, such as tissue, skin, cell membrane or cartilage. Thus, the use of different GAG compositions contemplated by the invention and, preparation thereof is within the ambit of the skilled artisan on the basis of the known composition of the specific tissue or cell type and then employing GAG in this invention which is similar to or the same as the GAG of the specific tissue or cell type.

As discussed above, in the pouch embodiments of the invention, cells may be placed within with nutrient added and expression product harvested from the exterior of the pouch. For instance, the 2–4 ml, most preferably about 300,000 to 1 million islet cells can be injected with nutrient media and insulin then harvested from the exterior. In an alternative embodiment, since islet cells are somewhat costly, known recombinants such as E. coli which express insulin (available from Hoechst AG) may be injected into the pouch with nutrient, with the insulin expression product harvested (preferably in vitro) from the pouch exterior, thereby minimizing antigenic contaminants from the E. coli and the need for purification steps in the processing of the expressed insulin. Suitable nutrient and amount thereof for such E. coli is easily determined by the skilled artisan from known techniques for growing E. coli, as well as from product information from the supplier.

Alternatively, the surface of a sheet of the composition of the invention can be used to grown cells for harvesting of the cells themselves. For instance, in the known preparations of lymphocytes and hybridomas for obtaining antibody-secreting cells, the cells can be grown on sheet composition of the invention or, on a pouch composition of the invention with nutrient within and absorbed to the cells.

Thus, with reference to FIG. 11, if pouch 5 is to be sealed at opening 29 cells may be within the pouch, with nutrient, with expression products therefrom harvested from the exterior surfaces of sheets 10 and 20. Cells may be within the pouch and nutrient placed on sheets 10 and 20, and after absorption into the pouch, expression products harvested from the exterior of sheets 10 and 20, preferably after washing any excess nutrient from sheets 10 and 20. In another alternative, cells and nutrient may be placed over the exterior of sheets 10 and 20 with expression product absorbed into the interior of pouch 5. The product is harvested by extraction thereof from the pouch interior.

Additionally, since by choice of membrane pore size may be varied, the inventive composition in sheet form may be used as a selective membrane for dialysis or other membrane-employing or filtration processes, either in vivo or in vitro, so as to allow for reduced contamination.

Further, as to in vivo applications, such as subcutaneous or internal applications, the inventive membrane composition in pouch form can also be used to deliver various compositions. For instance, time-release pharmaceutical or medicinal compounds may, in suitable dosage, be administered via the pouch of the invention, in the manner that such compounds are presently administered by injection or, by transdermal means, again, taking into consideration typical factors such as the age, weight, sex, and general condition of the individual to receive administration. Also, vaccine or immunological preparations can be administered via the pouch of the invention. For instance, live typhoid vaccine preparations require multiple doses over about 3 days to a week. Placement of such a preparation in a pouch of the invention with time release secretion of antigen allows the antigen to be delivered to the host, without excessive administration or, administration of the disease causing agent itself. Further, recombinant cells which express the antigen, either by having a plasmid inserted therein which has DNA coding for the antigen (e.g., either mammalian or bacterial cells having such a plasmid) or by recombinant viral infection of sail cells, can be placed within the pouch for harvesting of the antigen or administration thereof, either in vitro or in vivo. In the in vitro embodiment, suitable nutrient is thus added to the cells.

Accordingly, the invention comprehends several utilities and embodiments. With these utilities and embodiments, the invention comprehends methods as well. For instance, the invention comprehends in vitro methods for culturing cells, harvesting product, or both, as discussed above, as well as in vivo methods of treating or controlling a condition or inducing an immunological response by implanting a pouch containing a suitable substance in an individual in need thereof. Of course, a particular embodiment of interest involves islet of Langerhans cells or other insulin-expressing cells and either in vitro methods for culturing such cells or harvesting insulin therefrom or, of treating or controlling diabetes by implantation of a pouch containing a sufficient quantity of such cells for expression of a sufficient quantity of insulin, in an individual in need thereof. The pouches of the invention can therefore by of any suitable size; however, a size of about 1×1 to 6×6 preferably about 2×2 to about 4×4 inches and a thickness (membrane sheet) of 5 to 50, preferably 10 to 40, more preferably 10, 20 or 40 micrometers, and 1 to 5, preferably 2 to 3 millimeters thick with a volume of about 1 to 10, preferably 2 to 8 ml. The sheets can also be produced in a chamber which is a container, preferably of plastic, preferably about 21×17×3 cm, which can be placed in a shaker such as a linear shaker with adjustable speed (e.g., 15–30 cycles per minute). In this manner membrane may be reacted, with mixture, with the bind moiety.

The following non-limiting Examples are given by way of illustration only and are not to be considered a limitation of this invention.

EXAMPLES

Example 1

Activation of the Cellulose Membrane by Divinyl Sulfone

Commercially available cellulose membrane pieces measuring 5×5 cm, each weighing 30–50 mg (dry weight) were thoroughly washed in distilled, deionized water and suspended, each, in 8 ml 0.5 M sodium carbonate, at pH 11. Commercially available divinyl sulfone was added dropwise while under continuous agitation, until 800 μL of total volume was completed (10% of initial liquid volume). This was carried out in a well ventilated hood, and the operator wore gloves due to the toxicity of divinyl sulfone.

This activation reaction was allowed to proceed, under agitation, for 1 to 6 hours, at room temperature. At 4 hours, the activation could be complete but, allowing it to continue for 6 hours was not harmful and could ensure better activation. After that, the activated membrane was treated with repeated washings using water. Ten washes could suffice. The activated membrane could be used immediately for the coupling reaction, or it could be stored in cold acetone for later use.

Example 2

Coupling of GAG to the Activated Membrane

The activated membrane from Example 1 was suspended in 8 ml of 0.5 M sodium carbonate, pH 11, containing GAG chondroitin-6-sulfate, as a solute. The concentration was from 40 to 150 mg/mL. A concentration of 100 mg/ml could be used for sufficient coupling with 5×5 cm and divinyl sulfone activated cellulose membrane. The mixture was maintained under agitation for a minimum 24 hours, at a temperature about 4° C. The coupled membrane was then subsequently washed with 0.5 M sodium carbonate and water. The excess active groups that might still be present on the cellulosic membrane were now blocked by suspension in a 0.5 M sodium carbonate solution containing 5% (v/v) 2-mercaptoethanol and kept agitated for 2 hours.

Finally, the membranes were repeatedly washed with 1.0 M sodium chloride and water until the membranes were free of salt. These membranes could be stored under water, with 0.02% sodium azide, or can be dried under acetone and stored dry.

The reaction scheme for the binding reactions between the binding moiety, divinyl sulfone and the cellulosic membrane and the binding reaction between the binding moiety, divinyl sulfone and the GAG is illustrated in FIG. 1.

Example 3

Activation of the Cellulose Membrane with Butane-Diol-Diglycidyl-Ether (BDE)

Membrane pieces of size 5×5 cm were washed with water and suspended in 0.6 N sodium hydroxide, 4 ml, containing 0.2% (w/v) sodium borohydride, under agitation.

An identical volume of BDE was added slowly, under continuous mixing; the mixture was left under agitation for at least 12 hours at room temperature. The activated matrix was then repeatedly washed with 0.1 M sodium chloride, HCl at pH 3 and water.

Example 4

Coupling of GAG to the Activated Membrane

Each activated membrane from Example 3 was suspended in 8 ml of sodium carbonate at pH 11, containing GAG namely chondroitin-6-sulfate at concentrations in the range 40–150 mg/ml (100 ml could be used for sufficient coupling). The suspension remained under agitation for 24 hours, at least at room temperature. Preferably the temperature was elevated between 30 and 70° C. to allow coupling of GAG to the activated membrane. At 50° C. coupling can be effected.

The membrane was subsequently washed with 0.1 M sodium chloride, HCl pH 3 and water. The activated membrane that remained unreacted was then blocked by reaction with 10 ml of 1.0 M ethanolamine, at pH 9.0, under agitation, for 6 hours. The coupled membrane was then repeatedly washed with 1.0 M sodium chloride and water.

The GAG-membranes might be stored under water containing 0.02% sodium azide, at 4° C., under acetone or in a dry storage.

In the above examples the given size of the membranes used can vary, and therefore volumes of reactants used could be changed accordingly.

Typical composition data for a coupled membrane were: 0.15 to 0.25 mg GAG coupled per 7–8 mg membrane material, i.e., approximately 2.0–3.4% by weight in the case of BDE activation and 0.40 mg/7–8 mg of membrane in the case of DVS activation, that is, each 5% by weight.

After activation and coupling, the membranes might become stiffer and more tear-resistant. This might, without wishing to be bound by any one particular theory, be due to a degree of self-coupling that takes place during the activation process.

In Examples 1 to 4, the free end of the binding moiety might react with another hydroxyl group in the cellulosic membrane. However, this additional reaction could, without necessarily wishing to be bound by any one particular theory, help control pore sizes in the membrane without affecting yield of GAG coupling or imunogenicity in any significant manner. On the other hand, self-coupling of GAG could not take place because, when GAG was added, excess coupling reagent had been removed by washing of the membrane which, at this step, was called the "activated" membrane.

The reaction scheme for the binding reaction between the binding moiety and the membrane and the binding reaction between the binding moiety and GAG is illustrated in FIG. 2. (The binding moiety was a di-epoxide or bis-oxyrane, 1,4-butanediol-di-glycidyl ether)

Example 5

Modification of GAG

In this Example a modified GAG structure is prepared. The modification takes place in a mild acid hydrolysis of chondroitin sulfate-4 or chondroitin sulfate-6 (CIS-4, CIS-6) which frees amino groups at position 2 of N-acetyl-galactosamine moieties in the GAG's. These now free amino groups can then act as nucleophiles in the coupling reaction with the activated membrane. The mild acid hydrolysis of GAG is a well known reaction to those versed in GAG chemistry.

This deacetylation procedure has been described by Y. Guo and H. E. Conrad, Anal. Biochem. 176, 96–104, 1989. Its adaptation for this Example is as follows: dissolve 50 mg chondroitin-sulfate in 1 ml of a mixture of hydrazine, at 70% in water, containing 1% hydrazine sulfate. The flask is sealed and let to react for 4 hours at 100° C. The reaction is interrupted by adding 2 ml of toluene, followed by vacuum evaporation. This procedure is repeated twice. The residue is then dissolved in water for further use. The resulting solution may be neutralized by dilute sulfuric acid if needed.

Example 6

Activation of the Membrane by Carbonyl-Diixidazole (CDI)

Membrane pieces from Example 5 measuring 5×5 cm, weighing each 30–50 mg (dry weight) are dehydrated by repeated washing in acetone/water, 30/70 (v/v), acetone/water, 70/30 (v/v), and dry acetone, respectively, in a hood.

To each membrane, 10 mL dry acetone was added and mixed with 500 to 1000 mg CDI for 1 hour in a hood. Excess solvent (CDI) is then subsequently decanted by several quick washes with ice-cold water. Membranes must be used immediately for coupling.

Example 7

Coupling GAG to Activated Membrane

Activated membrane from Example 6 is suspended in 8 mL of 0.5 M sodium carbonate, pH 10, containing from 40 to 100 mg/mL (CIS-4, CIS-4 or mixtures thereof that had been previously subjected to a mild acid hydrolysis to free a portion of the amino groups at position 2 of N-acetyl-galactosamine moieties). These react with the activated matrix and form a stable carbamate linkage:

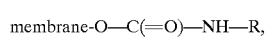

wherein R represents the remainder of GAG structure.

The mixture is stirred for at least 24 hr at 4° C. to allow coupling to be completed. The stirring is continued for an additional 6 to 10 hr to hydrolyze active groups that have not been coupled to GAG.

The membrane is washed in 1 M sodium chloride, and then in water, and store the membrane dry or under a solution at pH near 7, with 0.02% sodium azide.

Figure 4:
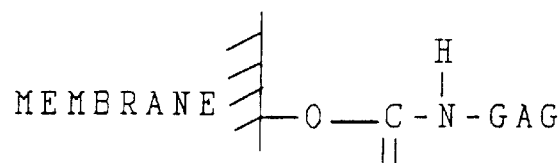
FIG. 4 shows a cellulosic membrane covalently bound to a binding moiety, an activated carbonyl, namely carbonyl di-imidazole, and the moiety also bound to GAG with the bonds being carbamate bonds.
Figure 5:
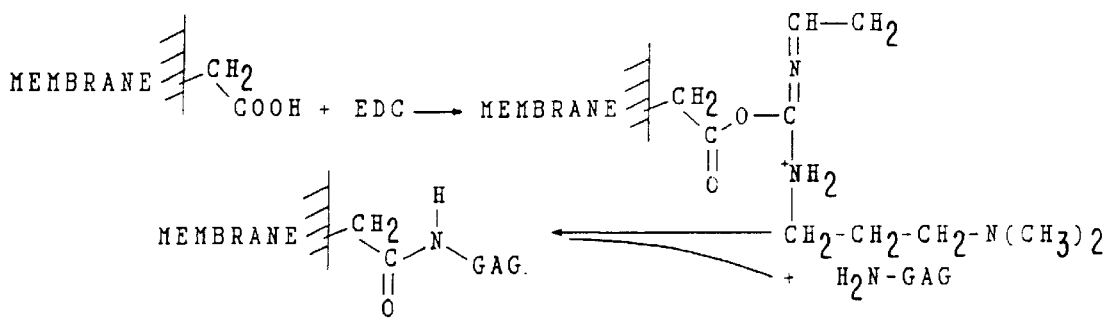
FIG. 5 shows a reaction scheme for the reaction of the cellulosic membrane covalently binding with to a binding moiety, a carbodiimide, an EDC, i.e., 1-ethyl-3-(3-dimethylamino-propyl)carbodiimide, $CH_3$—$CH_2$—N=C=N—$CH_2$—$CH_2$—$CH_2$—$N(CH_3)_2$, and with GAG covalently wherein the bonds are amide bonds.
Figure 6:
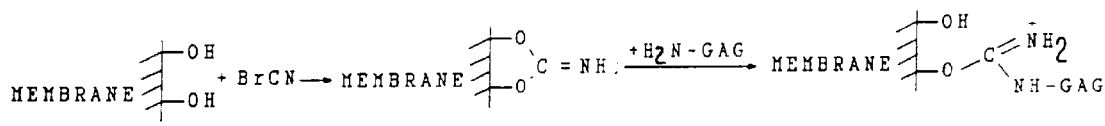
FIG. 6 shows a reaction scheme for the reaction of the cellulosic membrane covalently binding with a binding moiety, cyanogen halide, i.e., cyanogen bromide, and with GAG covalently.
Figure 7:
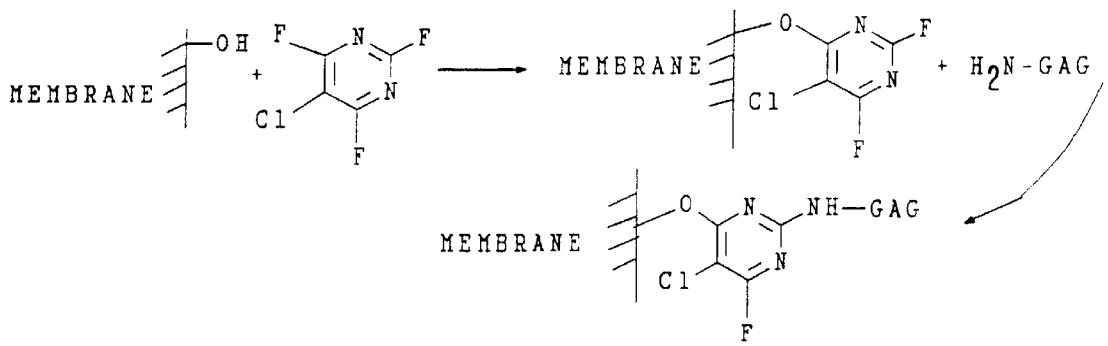
FIG. 7 shows a reaction scheme for the reaction of the cellulosic membrane covalently binding with a binding moiety, 2,4,6-trifluoro-5-chloropyrimidine, or FCP, and with GAG covalently, wherein the bonds are ether (to membrane) and carbamate (to GAG), showing that a mixture bonds and a mixture of moieties are permitted.
Figure 8:
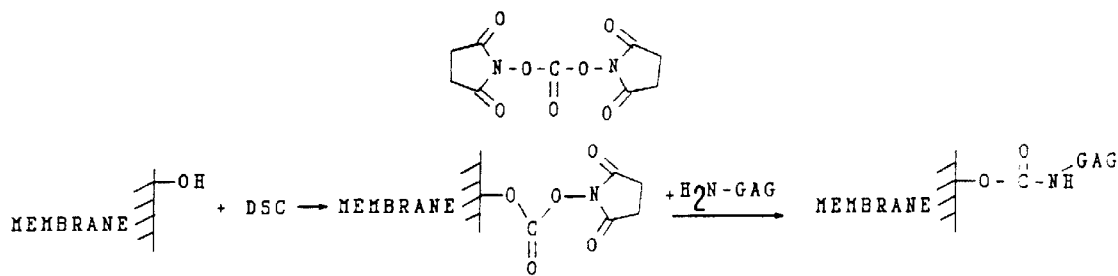
FIG. 8 shows a reaction scheme for the reaction of the cellulosic membrane covalently binding with a binding moiety, N,N'-disuccinimidyl-carbonate, or DSC, and with GAG covalently using ester bonding.
Figure 9:
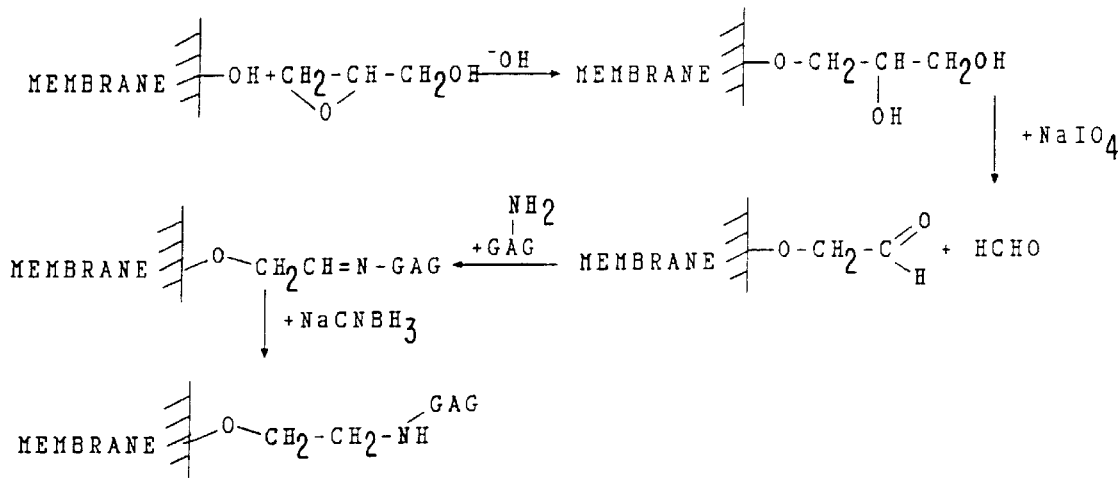
FIG. 9 shows a reaction scheme for a glycidol reaction among the cellulosic membrane, the binding moiety, and the GAG.
Figure 10:
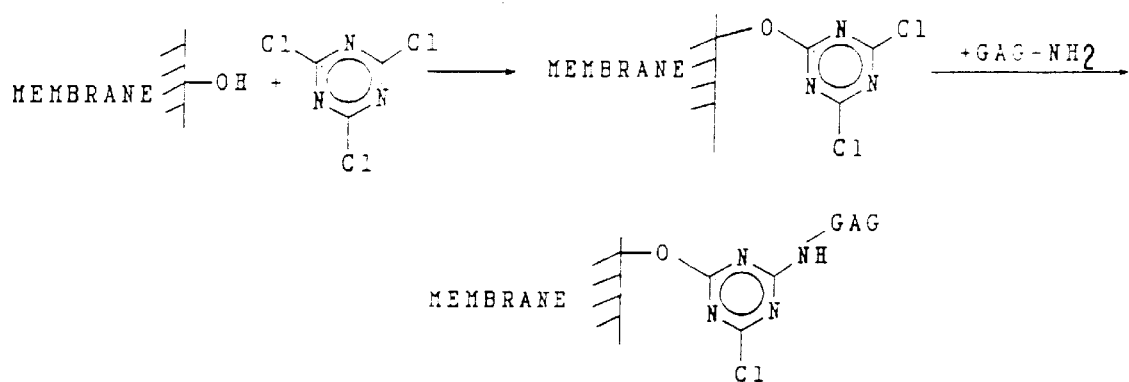
FIG. 10 shows a reaction scheme for the reaction of the cellulosic membrane covalently binding with the binding moiety, a cyanuric halide, i.e., a cyanuric chloride, namely trichloro-5-triazine, and with GAG using ether bonds.

The reaction scheme for the binding reaction between the binding moiety and the cellulosic membrane and the binding reaction between the binding moiety and GAG is illustrated in FIG. 3. A carbamate bond (illustrated in FIG. 3) is formed between membrane hydroxyl, carbonyl, and amino group of deacetylated GAG as illustrated in FIG. 4.

Example 8

Preparing Modified Activated Membrane

In this Example, the membranes are chemically modified to contain carboxy-methyl groups ($-CH_2-COOH$) such that these are now able to form amide bonds with a GAG bearing free amino groups, as in Examples 5–7. Carboxymethylation of the membrane is done by reacting with chloroacetic acid, in a strong alkaline medium. This is a well-known process to those well versed in chemical reactions related to preparation of affinity chromatography materials. The coupling method used are similar to those used in preparing "affinity chromatography" columns and materials, as described by Dean, Johnson and Middle in "Affinity Chromatography—A Practical Approach", IRL Press, Washington, D.C., 1985, Ch. 2, p.31–59, or as described in Scouten in "Affinity Chromatography; bioselective adsorption on inert matrices", John Wiley & Sons, New York, 1981, Ch. 2 and 3, p. 20–84.

Example 9

Coupling GAG to Membranes Containing Carboxyl Groups

Membrane pieces from Example 8 measuring 5×5 cm, each weighing 30–50 mg are suspended in 10 mL water at pH 4 each containing 40 mg of recently dissolved 1-ethyl-3-(3-dimethylaminopropyl) carbodiimide (EDC). To this, add 200–500 mg GAG modified from Example 5 and 8 which contains free amino groups in the minimum possible volume, also at pH 4, and the mixture is stirred at room temperature for 1 hour. The liquid phase is removed and the membranes are washed with 500 mL water in 50 mL portions. The pH is adjusted to about approximately 7 and stored in the refrigerator with 0.02% sodium azide or, alternatively, store in the dry state.

Having thus described in detail preferred embodiments of the present invention, it is to be understood that the invention defined by the appended claims is not to be limited by particular details set forth in the above description as many apparent variations thereof are possible without departing from the spirit or scope thereof.

What is claimed is:

1. A non-immunogenic biocompatible macromolecular membrane sheet composition comprising: a non-immunogenic biocompatible macromolecular cellulosic membrane sheet having covalently bound to its surface a chondroitin sulfate through a binding moiety selected from the group consisting of divinyl sulfone and butanediol-diglycidyl ether, wherein the binding moiety is covalently bound to a carbon or an oxygen of the cellulosic membrane sheet by an ether bond or an ester bond, and is covalently bound to a carbon, an oxygen, or a nitrogen of the chondroitin sulfate by an ether bond or an ester bond; and, the cellulosic membrane sheet is reinforced, and the non-immunogenic biocompatible macromolecular membrane sheet composition has a pore size or permeability of less than about 100,000 daltons.

2. The composition of claim 1 wherein the chondroitin sulfate is chondroitin-4-sulfate.

3. The composition of claim 1 wherein the chondroitin sulfate is chondroitin-6-sulfate.

4. A pouch comprising the composition of claim 1.

5. A surface for culturing cells in vitro comprising the non-immunogenic biocompatible macromolecular composition of claim 1.

6. A surface for culturing cells in vitro comprising the pouch of claim 4.

7. The composition of claim 1 wherein the binding moiety is butanediol-diglycidyl ether (BDE).

8. The composition of claim 1 wherein the binding moiety is divinyl sulfone.

9. The composition of claim 1 prepared by a process comprising the following steps in the sequence set forth:

activating the cellulosic membrane sheet by reacting said membrane sheet with the binding moiety to form an activated membrane sheet, and reacting said activated membrane sheet with the chondroitin sulfate.

10. The composition of claim 9 wherein the chondroitin sulfate is chondroitin-4-sulfate.

11. The composition of claim 9 wherein the chondroitin sulfate is chondroitin-6-sulfate.

12. A pouch comprising the composition of claim 9.

13. A surface for culturing cells in vitro comprising the non-immunogenic biocompatible macromolecular membrane sheet composition of claim 9.

14. A surface for culturing cells in vitro comprising the pouch of claim 12.

15. The composition of claim 9 wherein the binding moiety is butanediol-diglycidyl ether (BDE).

16. The composition of claim 9 wherein the binding moiety is divinyl sulfone.

17. A method of making a non-immunogenic biocompatible macromolecular membrane composition comprising the following steps in the sequence set forth:

activating a cellulosic membrane sheet by reacting said membrane sheet with a binding moiety selected from the group consisting of divinyl sulfone and butanediol-diglycidyl ether to form an activated membrane sheet, and reacting said activated membrane sheet with a chondroitin sulfate.

* * * * *